United States Patent
Fredriksson et al.

(10) Patent No.: US 10,843,009 B2
(45) Date of Patent: Nov. 24, 2020

(54) METHOD, COMPUTER PROGRAM PRODUCT AND COMPUTER SYSTEM FOR RADIOTHERAPY TREATMENT PLANNING

(71) Applicant: RaySearch Laboratories AB, Stockholm (SE)

(72) Inventors: Albin Fredriksson, Stockholm (SE); Rasmus Bokrantz, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 133 days.

(21) Appl. No.: 16/091,618

(22) PCT Filed: Apr. 5, 2017

(86) PCT No.: PCT/EP2017/058081
§ 371 (c)(1),
(2) Date: Oct. 5, 2018

(87) PCT Pub. No.: WO2017/174643
PCT Pub. Date: Oct. 12, 2017

(65) Prior Publication Data
US 2019/0117997 A1    Apr. 25, 2019

(30) Foreign Application Priority Data

Apr. 8, 2016  (EP) .................................... 16164469

(51) Int. Cl.
*A61N 5/00* (2006.01)
*A61N 5/10* (2006.01)
*G16H 20/40* (2018.01)

(52) U.S. Cl.
CPC ......... *A61N 5/1037* (2013.01); *A61N 5/1031* (2013.01); *G16H 20/40* (2018.01)

(58) Field of Classification Search
CPC ..... A61N 5/1037; A61N 5/2031; G16H 20/40
See application file for complete search history.

(56) References Cited

FOREIGN PATENT DOCUMENTS

| EP | 2 878 338 A1 | 6/2015 |
| WO | WO-2006/130771 A2 | 12/2006 |
| WO | WO-2011/154853 A1 | 12/2011 |

OTHER PUBLICATIONS

Riboldi et al., "Challenges and opportunities in image guided particle therapy," 2015, 37th Annual International Conference of the IEEE Engineering in Medicine and Biology Society, pp. 5227-5230. (Year: 2015).*
Bohoslavsky, Román, et al., "Probabilistic objective functions for margin-less IMRT planning," Phys. Med. Biol. 58 (2013) pp. 3563-3580.
Gordon, J. J., et al., "Coverage optimized planning: Probabilistic treatment planning based on dose coverage histogram criteria," Med. Phys. 37 (2), Feb. 2010, pp. 550-563.

\* cited by examiner

*Primary Examiner* — Kiho Kim
(74) *Attorney, Agent, or Firm* — Faegre Drinker Biddle & Reath LLP

(57) ABSTRACT

A scenario-based radiotherapy treatment plan optimization method is used to define an extended region of interest for treatment planning purposes, based on the union of the positions of a region of interest in a number of different scenarios, each scenario representing a realization of a possible location of the region of interest. Preferably a number of scenarios are defined and some of these scenarios are used to define the extended region.

7 Claims, 1 Drawing Sheet

METHOD, COMPUTER PROGRAM PRODUCT AND COMPUTER SYSTEM FOR RADIOTHERAPY TREATMENT PLANNING

This application is the National Stage of International Application No. PCT/EP2017/058081, filed Apr. 5, 2017, and claims the benefit of European Patent Application No. 16164469.5, filed Apr. 8, 2016, the entire contents of which are incorporated by reference herein.

TECHNICAL FIELD

The present invention relates to a method for radiotherapy treatment planning.

BACKGROUND AND RELATED ART

Radiotherapy involves delivering a radiation dose to a target organ, typically a tumour. Typically, radiotherapy treatment planning involves optimizing the plan to achieve one or more set goals. The aim is to deliver a precise dose, or a minimum dose, to the target while minimizing the dose to surrounding tissue and organs. The target is often referred to in planning as a clinical target volume (CTV).

Usually, the position of the tumour cannot be determined with exact precision as it will depend on the patient's position, movements occurring within a fraction, for example because of breathing, and also changes to the patient geometry that happen between fractions. The tumour position uncertainty is usually represented by a number of scenario, each representing a possible tumour location.

To account for this, a planning target volume PTV may be defined, encompassing the CTV and providing a margin around it. To ensure a specific coverage probability of a CTV, a dose-volume histogram (DVH) criteria may be applied to the PTV. Typically, a minimum DVH criterion is set stating that a certain percentage of the PTV should receive at least a minimum dose. Further DVH criteria may be set stating maximum doses for other tissues or organs. However, since it is the dose to the whole PTV that is monitored, there is no guarantee that a sufficient dose is actually delivered to the CTV, which is a subset of the PTV. A DVH criterion can be satisfied for the PTV even if the CTV within the PTV is underdosed, which could even imply 0% probability of CTV coverage.

In Gordon, Sayah, Weiss, and Siebers (2010), Coverage optimized planning: probabilistic treatment planning based on dose coverage histogram criteria, the intention is to solve a similar problem: achieving a probability of a specific target coverage. In short, this article describes an alternative way of providing margins around the CTV. The voxels that are to be penalized are selected directly on the basis of the voxel doses: in each iteration, a lower dose level ld is determined, and all voxels for which the dose d satisfies ld<=d<=ud are penalized, where ud is the desired minimum dose. This means that the correlation between voxels in different scenarios is not taken into account.

In Bohoslavky, Witte, Janssen, van Herk (2013), Probabilistic objective functions for margin-less IMRT planning, a similar method is used for evaluating the CTV objective under various scenarios, sorting the CTV objective values, and neglecting scenarios with values above a certain threshold. Then, the expectation of the CTV objective is optimized. Stated in more mathematical terms, they optimize the expected CTV objective value conditioned on that its value will be less than the value-at-risk at a certain level (typically 5%). This means that the dose to each of the included voxels is weighted according to in how many scenarios the voxels are contained in the CTV and the probability of these scenarios. Consequently the dose distribution is likely to decrease gradually from the center of the region of interest towards the edge, resulting in some voxels receiving a dose that is too low for therapeutic purposes but still harmful to the tissue.

SUMMARY OF THE INVENTION

It is therefore an object of the invention to improve treatment planning to deliver radiation more precisely to a CTV.

The invention relates to a method of radiotherapy treatment planning comprising a method of radiotherapy treatment plan optimization using a scenario-based optimization function to perform optimization based on at least a first and a second scenario, each scenario representing the realization of at least one uncertainty related to the position of at least one region of interest, the method comprising the steps of
   providing input data for optimization;
   defining at least a first and a second scenario, the first and second scenario representing a first and a second realization, respectively, of the at least one uncertainty, including a first and a second possible location of the region of interest;
   identifying the extent of the region of interest in the first scenario and in the second scenario;
   defining the extended region of interest volume based on the union of the extent of the region of interest in the first and the second scenario;
   optimizing a radiotherapy treatment plan using the extended region of interest volume.

Methods according to the invention therefore ensure that the region of interest is covered for all scenarios, that is, regardless of which scenario actually occurs. At the same time, locations where the region of interest cannot be located are not included in the extended region of interest, which means they will not unnecessarily receive a radiation dose.

Preferably the method further comprises the following steps:
   defining at least a third scenario representing a third realization of the at least one uncertainty, including a third possible location of the region of interest,
   evaluating the scenarios according to a quality measure
   selecting at least two of the at least three scenarios having the best quality measure
   identifying the extended region of interest volume based on the union of the selected at least two scenarios.

In this case, unfavourable scenarios, or scenarios that are unlikely to occur may be discarded and the extended region of interest will be defined based only on the selected scenarios.

The optimization of the radiotherapy treatment plan may include setting a minimum dose or DVH criterion for the extended region of interest volume. This is typically done if the region of interest is a target that should be treated.

According to the invention, dose optimization is based on a criterion, the fulfillment of which gives a probabilistic guarantee on coverage. Unlike a conventional PTV, the method allows for the inclusion of scenario probabilities when determining which voxels to neglect. The method moreover retains the geometric voxel dependence and values all included voxels identically because it does not use the expectation of the objective. Unlike the method proposed by Bohoslaysky, no voxel will receive a weighted reduced dose based on its probability. Instead, the dose will be the same for all voxels within the extended target as identified. This increases the chance that the prescribed dose is actually delivered to the clinical target volume CTV.

The term "based on the union" may mean the union of the possible extents of the region of interest with no modifications. It may also mean the union subjected to some sort of smoothing function to provide even contours, or processed in another suitable way. Preferably, the number of scenarios is selected such that the union has a sufficiently smooth contour to be suitable for treatment planning without any further processing.

The region of interest may also be an organ at risk. If an organ at risk is considered as a region of interest, the optimization includes defining an extended organ at risk volume based on all the possible locations of the organ at risk and setting a maximum dose or DVH criterion for the extended organ at risk volume. The optimization method may also take into account two or more regions of interest, for example, one target and one organ at risk. In this way alternatives for possible locations of several regions of interest can be evaluated together as a whole. This means that the scenarios selected may be the ones fulfilling the combined goals of target coverage and protection of an organ at risk, rather than the scenarios that are best with regards to one of these goals. The scenarios may also include material properties, such as attenuation. In the case of ion therapy, material properties such as the attenuation may affect how deeply into the patient the ions will penetrate. This may be translated into corresponding different positions of the target in the direction of the beam. Therefore, scenarios including these different material properties may also be defined and processed according to the principles defined in this document.

The maximum or minimum dose or DVH criteria may be set in any suitable way, as the skilled person is aware. For example, the one-sided square deviation of the dose from the prescription dose may be used. Alternatively, the greatest one-sided linear deviation of the dose from the prescription dose may be used.

The invention also relates to a computer system for performing dose calculations for radiotherapy, the system comprising processing means, said computer system having a program memory having stored therein a computer program product according to the above, in such a way that the computer program product, when executed, will control the processing means.

Aspects of the invention also relate to a computer program product including computer readable code means which when run in a processor will cause the processor to perform the method according to an embodiment of the invention. Aspects of the invention relate to a non-transitory computer-readable medium encoded with computer-executable instructions which when run in a processor will cause the processor to perform the method.

Aspects of the invention also relate to a computer system for performing dose calculations for radiotherapy treatment planning, the system comprising processing means, said computer system having a program memory having stored therein a computer program product according to the above in such a way that the computer program product, when executed, will control the processing means to perform a method according to an embodiment of the invention.

BRIEF DESCRIPTION OF THE DRAWINGS

In the following the invention will be described in more detail and with reference to the drawings, in which.

DETAILED DESCRIPTION OF PREFERRED EMBODIMENTS

The planning according to the invention may be performed with respect to a target that is to receive at least a minimum dose, but it may also be performed with respect to another type of region of interest, such as an organ at risk, for which the dose should be kept as low as possible, or below a maximum dose. When the term "target" or "CTV" is used in the description it should be kept in mind that the organ concerned could be any type of region of interest.

Figure 1:
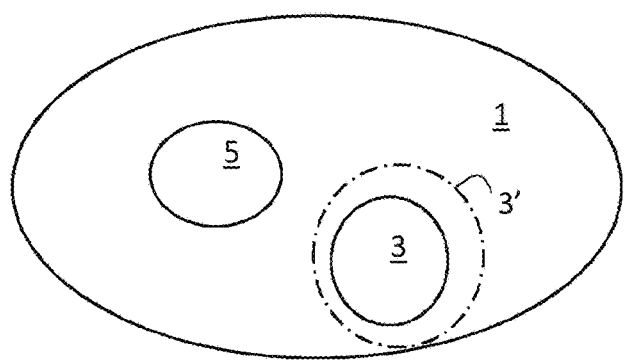
FIG. 1 illustrates an image of a patient including a CTV with a PTV around it according to the prior art

FIG. 1 shows a schematic image of a patient 1. Although this image is shown in two dimensions, it should be noted that images used for treatment planning are usually 3D images. The image includes a CTV 3, which is the target that is to be treated with radiotherapy. In general, the dose should be minimized everywhere outside of the CTV, although there may also be one or more particularly sensitive regions, often called organs at risk, OAR, for which it is particularly important to minimize the dose. In FIG. 1, one OAR 5 is shown.

To ensure that the entire CTV receives the desired dose even if the patient is not correctly positioned relative to the apparatus, a margin is applied around the CTV shown in FIG. 1 as a dash-dotted line 3'. In the simplest case this margin is applied as a fixed number of voxels outside of the CTV around the whole volume of the CTV. The margin may also take into account the presence of an organ at risk, as shown in FIG. 1, where a narrower margin is applied on one side of the CTV to avoid giving a too high dose to the organ at risk.

Figure 2:
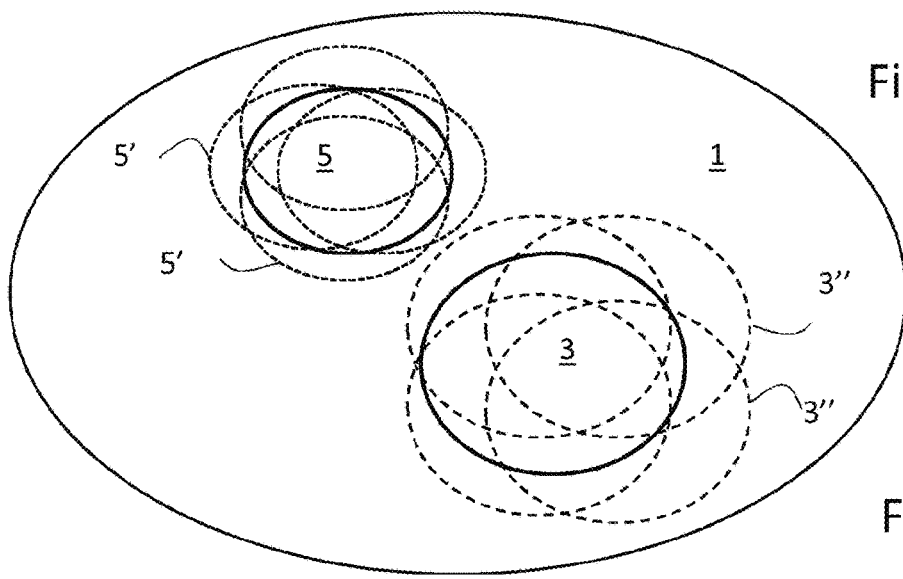
FIG. 2 illustrates an example of a patient including a CTV and an organ at risk with extended volumes determined according to embodiments of the present invention

FIG. 2 illustrates the same patient as in FIG. 1, with the same CTV 3 and the same OAR 5, shown as solid outlines. In FIG. 2, however, a number of scenarios for possible locations of the CTV and OAR are shown.

As illustrated in FIG. 2, instead of applying a fixed margin around the CTV, the margin may instead be determined by applying different scenarios for the possible location and shape of the tumour. FIG. 2 shows a number of dashed circles 3'' grouped around the target 3, each corresponding to a possible location of the target 3 in at least one scenario. For visibility, only four dashed circles are shown in FIG. 2 although the number of scenarios will normally be higher, to obtain a smooth outline of the extended CTV. The number of scenarios may be selected as is found to be suitable. The scenarios may also include possible location and shape of other organs or tissues, including one or more organs at risk. This is indicated in FIG. 2 by a number of dotted shapes 5' grouped around the organ at risk 5, each corresponding to a possible location of the organ at risk 5. Each scenario will take into account one possible location of the target 3 and may also consider a possible location of the organ at risk 5 and other organs or tissues. For each scenario a quality measure is determined. For example, the minimum dose function may be evaluated on the CTV for each scenario. A number of the scenarios is selected for treatment planning, for example as a percentage of the scenarios. The percentage selected must be higher than O % and up to and including 100%. An extended volume for the CTV (or other region of interest) will be determined based on its location in all of the selected scenarios and will be referred to as an extended treatment volume. In the simplest case, the union of all dashed circles 3" is taken as the extended treatment volume. Similarly, the union of all dotted shapes 5' is taken as the extended organ at risk volume.

Ideally, the number of scenarios, and the scenarios themselves, are selected such that the union of all possible locations of a particular organ forms a shape that has a smooth outline to facilitate treatment planning.

Figure 3:
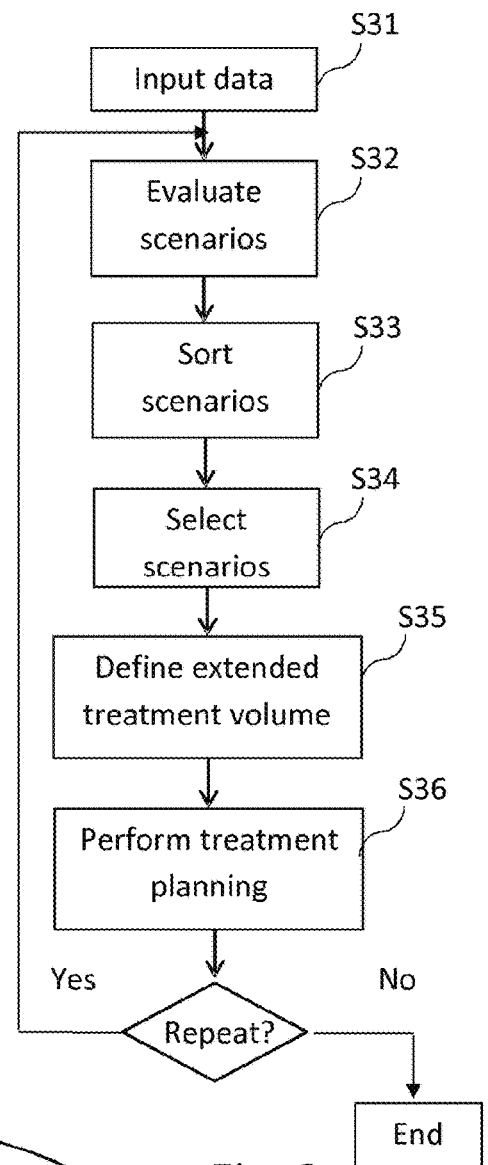
FIG. 3 is a flow chart of a method according to an embodiment of the invention FIG. 4 discloses schematically a computer system that may be used for performing the invention

FIG. 3 is a flow chart of an embodiment of the inventive method. Input data provided in step S31 include patient data including a clinical target volume CTV and/or an OAR. Input data may also include information about different scenarios, and one or more coverage probability criteria to be applied in the optimization. In a second step S32 a minimum dose function for the CTV and/or a maximum dose function for an organ at risk, is evaluated under a number of scenarios. Typically, scenario doses are calculated using rigid translation and/or rotation of the dose, that is, assuming the static dose cloud approximation, but the scenario doses could also be calculated more accurately. Each scenario includes details about a possible location, size, etc. of the CTV, and/or the patient's material properties such as density for the CTV and/or other portion of the patient. The scenario may also include possible location, size etc. of one or more other organs or tissues, such as an organ at risk, and of the patient as a whole.

In step S33 the scenarios are sorted according to a quality measure. If the scenarios only include information about the CTV, the minimum dose function values may be used. If the scenarios include information about one or more other organs or tissues as well a quality measure based on both the CTV and the other organ is preferably used. This may include a minimum dose function for the CTV and a maximum dose function for an organ at risk. The quality measure may also be determined as one or more DVH functions, or by combinations of other functions used in treatment planning.

In step S34 a percentage of the best scenarios is selected. The percentage must be greater than 0 but may include all of the scenarios. Optionally the probability that each of these scenarios will occur is determined and used in the selection. For example, scenarios that involve a small change in the location of the target, or other organ, may be considered more likely to occur than scenarios involving a greater change. In this case the most probably scenarios may be selected.

In step S35 the extended treatment volume is identified based on these selected scenarios while the poorest scenarios are discarded. This is achieved by translating the CTV and/or OAR voxels according to the scenarios and defining the extended treatment volume as the union of the CTV voxels, and OAR voxels, respectively, of the selected best scenarios. The extended treatment volume therefore corresponds to the union of all, or a selected fraction of the possible locations 3" of the CTV in FIG. 2. Similarly, the extended OAR volume corresponds to the union of possible locations 5' of the OAR. This step can be performed also taking the probability of the scenarios occurring into account.

In step S36 the treatment planning is performed. This usually involves applying a minimum dose function to all the voxels identified in step S35 as included in the extended treatment volume. The minimum dose function prescribes a certain minimum dose to these voxels. The minimum dose function evaluates a one-sided (positive) difference between the prescribed dose and the doses in the CTV voxels, as discussed above. It may also involve applying a maximum dose function to all the voxels included in an extended volume of an organ at risk, corresponding to the organ 5 of FIG. 2.

In the optimization that is performed as part of treatment planning, the evaluation of the optimization functions may result in a change in which scenarios are considered to be the best ones. Hence, the optimization is an iterative process in which the set of scenarios on which the extended treatment volume and/or the extended organ at risk volume is based may change. Therefore, the respective extended volumes may change during the treatment planning. In step S34, any number of scenarios between 0 and all scenarios might be selected. Preferably, however, a majority of the scenarios are selected, for example the best 90% or the best 95%. In this case 10% or 5%, respectively, of the scenarios are discarded. The union of the CTVs in all the selected scenarios defines a volume in the body corresponding to the CTV and a margin. In this case, the margin corresponds to the outline of the possible locations of the CTV in the selected scenarios. It would also be possible to base the extended treatment volume and/or the extended volume of an organ at risk on all of the scenarios, that is, to let the set of selected scenarios include all scenarios. This means that steps S34 and S35 are optional.

It should be noted that depending on the result in step S36, a new set of scenarios may turn out to be the best scenarios. In this case, the method may be performed again using a union of voxels based on the new set of scenarios to determine a new extended treatment volume and/or a new extended organ at risk volume.

Figure 4:
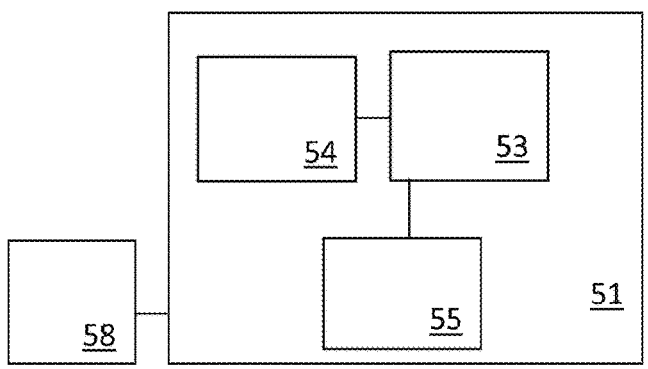

FIG. 4 is a schematic representation of a computer system in which the inventive method may be performed. A computer 51 comprises a processor 53, a data memory 54 and a program memory 55. Preferably, a user input means 58 is also present, in the form of a keyboard, a mouse, a joystick, voice recognition means or any other available user input means.

The data memory 54 holds input data for the method. The type of input data depends on the embodiment. Input data may include a treatment plan, patient data, one or more value sets and one or more objective functions, as well as the scenarios to be considered during optimization. The data in the data memory 54 may be generated in the computer 51, entered by means of the user input means 58 or received from another storage means, in any way known in the art.

As will be understood, the data memory 54 is only shown schematically. There may be several data memory units, each holding one or more different types of data, for example, one data memory for the value set, one for the objective function, etc.

The program memory 55 holds a computer program arranged to be run in the processor 53 to control the processor to perform the optimization. It will be understood that not all of the steps of the method of the flowchart of FIG. 2 are necessarily performed in the computer 51.

The invention claimed is:

1. A method of radiotherapy treatment plan optimization using a scenario-based optimization function to perform optimization based on at least a first and a second scenario, each scenario representing the realization of at least one uncertainty related to the position of at least one region of interest, the method comprising the steps of:

providing input data for the optimization;

defining at least a first and a second scenario, the first and second scenario representing a first and a second realization, respectively, of the at least one uncertainty, including a first and a second possible location of the region of interest;
identifying the extent of the region of interest in the first scenario and in the second scenario;
defining the extended region of interest volume based on the union of the extent of the region of interest in the first and the second scenario;
optimizing a radiotherapy treatment plan using the extended region of interest volume.

2. The method according to claim 1, further comprising
defining at least a third scenario representing a third realization of the at least one uncertainty, including a third possible location of the region of interest;
evaluating the scenarios according to a quality measure;
selecting at least two of the at least three scenarios having the best quality measure;
identifying the extended region of interest volume based on the union of the selected at least two scenarios.

3. The method according to claim 1, wherein the optimization of the radiotherapy treatment plan includes setting a minimum dose or DVH criterion for the extended region of interest volume.

4. The method according to claim 1, wherein the optimization of the radiotherapy treatment plan includes setting a maximum dose or DVH criterion for the extended region of interest volume.

5. The method according to claim 1, wherein each scenario further includes a possible location of a further region of interest, the optimization further including defining an extended volume for the further region of interest based on all the possible locations of the further region of interest and setting a maximum dose or DVH criterion for the extended volume for the further region of interest.

6. A computer program product comprising a non-transitory computer readable medium encoded with computer-executable instructions which when run in a processor will cause the processor to perform the method according to claim 1.

7. A computer system for performing dose calculations for radiotherapy, the system comprising a processor, said computer system having a program memory having stored therein a computer program product according to claim 6 in such a way that the computer program product, when executed, will control the processor.

* * * * *